United States Patent [19]

Latimer

[11] Patent Number: 4,956,506
[45] Date of Patent: Sep. 11, 1990

[54] VAPOR-PHASE HYDRATION OF OLEFINS TO ALCOHOLS IN SERIES REACTORS WITH INTERMEDIATE ALCOHOL REMOVAL

[75] Inventor: Edward G. Latimer, Ponca City, Okla.

[73] Assignee: Conoco Inc., Ponca City, Okla.

[21] Appl. No.: 454,796

[22] Filed: Dec. 21, 1989

[51] Int. Cl.⁵ .................. C07C 29/04; C07C 31/08; C07C 31/10
[52] U.S. Cl. .................. 568/899; 568/895; 568/896
[58] Field of Search .................. 568/899, 896, 895

[56] References Cited

U.S. PATENT DOCUMENTS

| | | | |
|---|---|---|---|
| 2,055,720 | 9/1936 | Francis | 568/899 |
| 2,130,669 | 9/1938 | Lewis | 568/898 |
| 2,313,196 | 3/1943 | Guinot | 568/899 |
| 2,729,682 | 1/1956 | Mottern | 568/899 |
| 3,950,442 | 4/1976 | Vogel et al. | 568/899 |
| 4,003,952 | 1/1977 | Foster et al. | 568/895 |
| 4,065,512 | 12/1977 | Carer | 568/899 |
| 4,180,688 | 12/1979 | Imaizumi et al. | 568/899 |
| 4,284,831 | 8/1981 | Okumura et al. | 568/899 |
| 4,307,257 | 12/1981 | Sada et al. | 568/899 |
| 4,327,231 | 4/1982 | Okumura et al. | 568/899 |
| 4,456,776 | 6/1984 | Neier et al. | 568/899 |
| 4,760,202 | 7/1988 | Dettmer et al. | 568/899 |
| 4,760,203 | 7/1988 | Carls et al. | 568/899 |
| 4,831,197 | 5/1989 | Henn et al. | 568/899 |
| 4,861,923 | 8/1989 | Olah | 568/899 |

Primary Examiner—J. E. Evans
Attorney, Agent, or Firm—Cleveland R. Williams

[57] ABSTRACT

A gas containing water vapor and a minor amount of ethylene and/or propylene is passed through several reactors in series containing a perfluorinated ion-exchange polymer catalyst to convert olefins to alcohols, and alcohol product is recovered from the effluent gases from each reactor.

19 Claims, 1 Drawing Sheet

VAPOR-PHASE HYDRATION OF OLEFINS TO ALCOHOLS IN SERIES REACTORS WITH INTERMEDIATE ALCOHOL REMOVAL

BACKGROUND OF THE INVENTION

Current commercial processes for making ethanol from ethylene operate at very high temperatures around 475°–600° F. in order to obtain suitable reaction rates. The catalyst used commercially is a phosphoric acid catalyst impregnated on a diatomaceous support, and the ethanol yields are around 6 percent.

The problem with vapor-phase hydration reactions of olefins to alcohol is that they are equilibrium limited. There is a maximum amount of alcohol which the vapor phase can hold before the reverse reaction, that is alcohol to olefin plus water, equals the alcohol formation. This maximum is usually about 5 to about 25 percent, depending on the temperature and pressure of the hydration reaction. The yields per pass are lower than the equilibrium amount, which makes the yields even smaller. To obtain an appreciable yield for the overall process, commercial vapor-phase hydration processes use recycle. This is expensive because of compressor costs and the larger reaction vessels which are required. Some processes use a mixed-phase reaction with liquid water so that the alcohol produced is continuously absorbed and the reaction is not equilibrium limited. Such processes get good yields per pass but require high water/olefin rates plus the alcohol/water solution in the reactor tends to dissolve the acid catalyst.

It would be desirable to have a process for the vapor-phase hydration of olefins to alcohols in which high yields of product can be obtained without the disadvantages of the existing commercial processes.

THE PRIOR ART

U.S. Pat. No. 2,130,669 to W. K. Lewis discloses the production of alcohols by the hydration of olefins. The process utilizes two reactors in series with product alcohols being recovered from each reactor. In one aspect in which alcohol product is not recovered from each reactor, the second reactor is maintained at a lower pressure than the first reactor.

BRIEF DESCRIPTION OF THE DRAWING

The drawing is a schematic diagram of a hydration reactor arrangement which illustrates the invention.

DETAILED DESCRIPTION OF THE INVENTION

Figure 1:
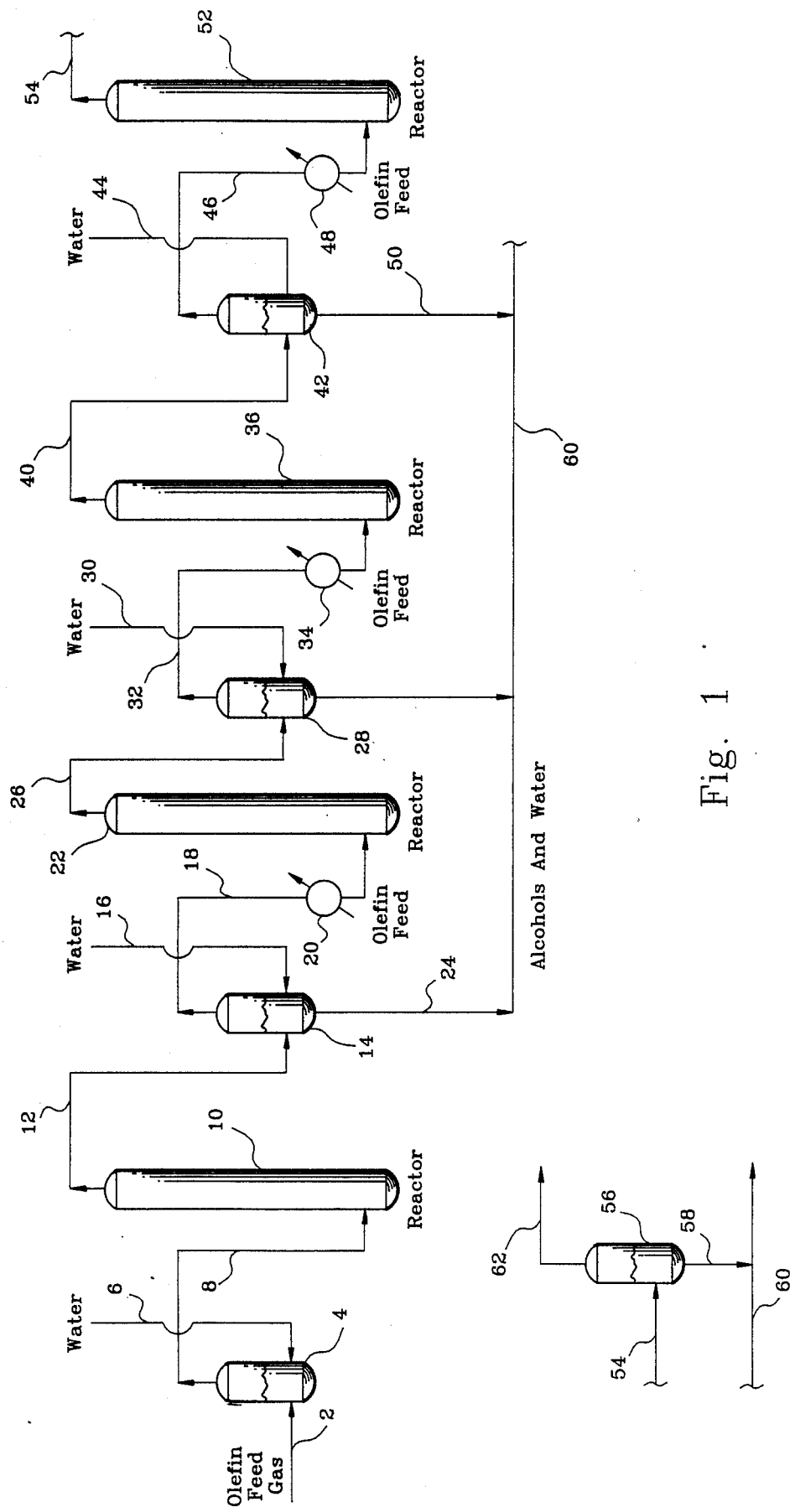

The invention may be described by reference to the hydration reactor configuration shown in the drawing. Referring to the drawing, olefin feed gas is introduced through line 2 to vessel 4, which contains a level of water. The feed gas is introduced below the surface of the water so that the gas leaving vessel 4 through line 8 is saturated or substantially saturated with water. As water is consumed in vessel 4 during the process, makeup water may be introduced to this vessel through line 6. The olefin feed gas containing water is introduced to hydration reactor 10, wherein it contacts a perfluorinated ion-exchange polymer catalyst, and a portion of the olefins in the feed gas is converted to the corresponding alcohols.

The olefin feed gas used in the process of the invention contains a minor amount of ethylene and propylene olefins, usually between about 5 and about 40 percent based on the total STREAM and more usually between about 10 and about 25 percent of total olefins. The major components of the gas feed are methane, hydrogen, and/or various other gases which are inert to the hydration reaction. Any suitable source of gases containing minor amounts of ethylene aned propylene may be used in carrying out the process. A particularly desirable gas is the tail gas from a fluid catalytic cracker. FCC tail gas usually contains from between about 10 and 20 weight percent ethylene and between about 4 and 10 weight percent propylene.

The catalysts employed in carrying out the process of the invention are perfluorinated ion-exchange polymers having a substantially fluorinated aliphatic (Teflon®) backbone with pendant sulfonic or carboxylic groups.

The catalyst composition of the process herein comprises a perfluorinated ion-exchange polymer containing sulfonic acid groups supported on an inert carrier having a hydrophobic surface with a mean pore diameter of at least 1000 Å. In particular the carrier comprises calcined shot coke.

The catalysts which are used in the processes of this invention are prepared by contacting the hydrophobic support with a solution of the sulfonic acid substituted perfluorinated ion exchange polymer, removing the axcess solvent to give a coated support, and activating the coated support by treatment with a strong mineral acid to give the supported catalyst.

The polymers that are applicable to this invention have structures that include a substantially fluorinated carbon chain that may have attached to it side chains that are also substantially fluorinated and contain sulfonic acid groups or derivatives of sulfonic acid groups. Such polymers for use in this invention have an equivalent weight of at least about 500. Preferably, the perfluorinated polymer contains a sufficient number of sulfonic acid groups to give an equivalent weight of from about 500 to about 20,000, and most preferably from about 900 to about 2,000. Although the polymer backbone comprises, for the most part, fluorinated carbon atoms, it is not necessary that all other atoms be excluded. For example, ether oxygen atoms may be present in the backbone, as well as in the side chains of the polymer. Such other atoms and/or groups as hydrogen (H), chlorine (Cl) and carboxy (COOH) may be present in limited amounts without significantly affecting the stability or operability of the polymer under process conditions. It is preferred that the polymer contain no greater than about 5 weight percent total of hydrogen and chlorine groups. Representative of the perfluorinated polymers suitable for use in the present invention are the Nafion ® polymers (a family of catalysts for use in the manufacture of industrial chemicals, commercially available from E. I. du Pont de Nemours and Company), and the polymers, or derivatives of polymers, disclosed in U.S. Pat. Nos. 3,282,875; 4,329,435; 4,330,654; 4,358,545; 4,417,969 and 4,610,762, which are hereby incorporated by reference.

Typically, suitable perfluorinated polymers are derived from sulfonylhalide group-containing polymers having a fluorinated hydrocarbon backbone chain to which are attached the functional groups or pendant side chains which in turn carry the functional groups. The pendant side chains can contain, for example,

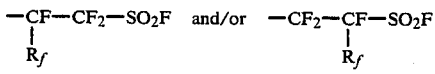

groups, wherein $R_f$ is F, Cl, or a $C_1$ to $C_{10}$ perfluoroalkyl radical. Ordinarily, the functional group in the side chains of the polymer will be present in terminal

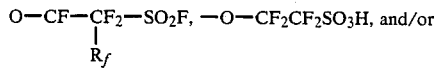

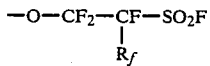

positions.

Although the fluorinated portion of the polymer molecule is in large part responsible for the desirable thermal stability of these polymers, it also contributes to the low solubility, and hence difficult processability, of these materials. However, it is possible to dissolve the polymer by heating it with an aqueous alcohol, particularly 50% aqueous ethanol, to about 250° C. or higher for several hours in a high pressure autoclave (Martin et al., Anal, Chem., Vol. 54, pp 1639–1641 (1982). Other solvents and mixtures may also be effective in dissolving the polymer. See, for example U.S. Pat. No. 4,433,082.

Ordinarily, for each part by weight of polymer employed to be dissolved, from as little as about 4 or 5 parts by weight up to about 100 parts by weight, preferably 20–50 parts by weight, of the solvent mixture are employed. In the preparation of the dissolved polymer, there is an interaction between the equivalent weight of the polymer employed, the temperature of the process, and the amount and nature of the solvent mixture employed. For higher equivalent weight polymers, the temperature employed is oridinarily higher and the amount of liquid mixture employed is usually greater.

The resulting mixture may be used directly, but it is preferred that the mixture be filtered through fine filters (e.g., 4–5.5 micrometers) to obtain clear, though perhaps slightly colored, solutions. The mixtures obtained by this process can be further modified by removing a portion of the water, alcohols and volatile organic by-products by distillation.

Commercially available solutions of perfluorinated ion-exchange polymers can also be used in the preparation of the supported polymer catalysts of the present invention (e.g., a 5 wt. % solution of a perfluorinated ion-exchange powder in a mixture of lower aliphatic alcohols and 10% water, Cat. No. 27,470–4, Aldrich Chemical Company, Inc., 940 West Saint Paul Avenue, Milwaukee, Wisconsin 53233).

The polymer can be deposited on the support by soaking the support in the liquid mixture containing the polymer and then removing any excess solvent. Typically, the coated support is dried at a temperature about the boiling point of the solvents for at least 1 hour. Alternatively, the supported polymer can be prepared by atomizing the coating solution in air in a sonic velocity nozzle and then laying the coating down on a particulate support in a highly turbulent mixing zone as described in U.S. Pat. No. 4,430,001, which is hereby incorporated by reference.

The thickness of the coating can be varied by adjusting the concentration of the polymer in the liquid mixture or by applying two or more layers of polymer onto the support. Suitable weight ratios of polymer-to-support vary from about 0.05 to about 3.0%. Higher weight ratios are possible, but less economic.

The composition of the support has been found to be important, however the properties that are considered most desirable for a carrier may vary in different applications. Properties that may be important in some situations include high surface area, high crush strength, high porosity, chemical resistance, thermal stability, and low cost. In all cases, the support must be resistant to the liquid composition of the polymer blend and to the temperatures used during the drying of the catalyst. For the catalysts used in the processes of this invention, it is also important the surface of the support be hydrophobic. Preferred supports with hydrophobic surfaces include polytetrafluoroethylene, copolymers of polytetrafluoroethylene and hexafluoropropylene, polyethylene, polypropylene and carbon in the form of coke.

A specifically preferred support is coke. "Coke" as used herein is the non-volatile residue of petroleum refining or coal distillation operations. Its composition depends on the source of the feedstock and the processing methods used. In general, it has a high C:H ratio and contains condensed, polynuclear aromatic compounds as well as organic and inorganic compounds of sulfur, nitrogen and metals such as vanadium, nickel, iron and copper. Coke includes a very broad range of hydrophobic materials including tar pitch coke, coke oven coke, needle coke, regular grade or anode coke, fuel grade coke, shot coke, speciality carbon cokes such gilsonite coke or others. Although the coke may be used in the green uncalcined form, it is preferable that the coke be calcined.

The most preferred support is calcined shot coke. Calcined shot coke alone is not a catalyst for hydrocarbon conversion reactions. The pore size range for conventional catalyst support material is between 50 and 600 Å. In contract, the mean pore diameter in calcined shot coke is in excess of 1000 Å, and the average surface area is 0.1–10.0 m²/g. It is unusual that a material with such large pores provides an effective support medium for catalysis. Calcined shot coke also has a very high crush strength. The preferred loading for calcined shot coke is 0.1–3.0%; higher loadings are possible, but are less cost-efficient. Thus any coating, even less than a monolayer coating of the polymer on the calcined shot coke results in a catalyst of high activity.

The supported perfluorinated ion-exchange polymers described herein can be used for hydrocarbon conversion reactions in continuous processes or in batch reactions.

Catalytic activity of the supported catalysts gradually decreases with use, but can be substantially restored by treatment with dilute acid, preferably 1N nitric acid, at about 80° C. In general, the integrity of the coated catalyst is maintained through many reaction cycles. The coating does not dissolve or flake off under the conditions of the hydrocarbon conversion reactions.

Preferably, the catalyst composition comprises from about 0.05 weight percent to about 5.0 weight percent, especially from about 0.05 weight percent to about 2.0 weight percent of a perfluorinated ion-exchange polymer containing sulfonic acid groups supported on the surface of an inert support having a hydrophobic surface with a mean pore diameter of about 1000 Å. Preferably the inert support is calcined shot coke.

The hydration of olefins to convert hydrocarbons to alcohols is an industrially important reaction that is often difficult to catalyze. In another process of this invention, the hydration of olefins is carried out by contacting in the presence of water and at a temperature of about 180° C. to about 250° C., an olefin chosen from the group of monoolefins containing 2 or more carbon atoms and a catalyst composition comprising from about 0.05 to about 5 weight percent, preferably from about 0.05 to about 2.5 weight percent of a perfluorinated ion exchange polymer containing sulfonic acid groups supported on an inert support having a hydrophobic surface with a mean pore diameter of about 1000 Å.

Usually the polymers employed as catalysts have an equivalent weight of at least about 500. Preferably, the polymers contain a sufficient number of sulfonic acid groups or carboxylic acid groups to give an equivalent weight from about 500 to about 20,000 and preferably from about 900 to about 2,000. Suitable perfluorinated ion-exchange polymers are known in the art and include the Nafion ® polymers available from Du Pont.

The hydration reaction is usually carried out at temperatures from about 250° to about 475° F. The preferred reaction temperatures for propylene are generally below those optimally used for the conversion of ethylene, thus propylene is preferably hydrated at a temperature from about 300° to about 375° F. and ethylene at a temperature from about 420° to about 475° F. The serial reactor arrangement of the process of this invention makes it convenient to utilize either a constant temperature in each reactor or different temperatures from reactor to reactor to optimize the conversion of propylene in certain reactors and ethylene in others.

Since elevated pressure favors the hydration reaction, the process is usually carried out at pressures substantially above atmospheric, e.g., from about 200 to about 4000 psig and preferably from about 600 to about 2000 psig.

The contact time of the olefin containing gas with the polymer catalyst will depend on the gas flow rate and the amount of catalyst used. The contact time of the gas with the catalyst is measured by the space velocity (WHSV). The WHSV in terms of cubic centimeters of total dry gas feed per minute per gram of polymer catalyst will usually be between about 1 and about 2000, and preferably between about 20 and about 100 for ethylene and 200 to 1000 for propylene.

It is important that the amount of water present during the hydration reaction exceeds that required to carry out the reaction. In the absence of water, the catalysts employed in the process begin to decompose at relatively low temperatures. For example, the Nafion ® catalysts in the absence of water start to decompose at 350° F., and decomposition proceeds rapidly above 400° F. When water is present, however, there is no decomposition of the catalyst at temperatures as high as 473° F. This is important, since it allows the hydration reaction to be carried out at higher temperatures, which are particularly significant for the conversion of ethylene to ethanol.

Saturation of the olefin containing feed gas by intimately contacting such gas with liquid water at hydration reaction conditions provides sufficient water in the gas feed to assure the presence of unreacted water during the hydration reaction. Contacting of the feed gas with water is effected by flowing the gas in the form of bubbles through a body of liquid water. The gas bubble size may be varied by passing the gas through small openings, such as those contained in a filtering element. Smaller gas bubbles usually will pick up more water than larger bubbles, thus providing a higher water content in the gas feed as it contacts the polymer catalyst.

The catalytic activity of the catalyst gradually decreases with use but can be substantially restored by treatment with dilute acid, preferably nitric acid, at about 175° F.

Referring again to the drawing, the hydration reaction of the olefins in the presence of water in reactor 10 converts from about 1 to about 25 percent of the ethylene and propylene to the corrosponding ethanol and isopropanol. Effluent gases from reactor 10 are passed through line 12 into vessel 14 where they are contacted with water. Alcohols in the gases are dissolved in the water and removed from vessel 14 through line 24. The remaining gases containing water are passed from vessel 14 through line 18 and into the second reactor 22. As necessary, makeup water may be added to vessel 14 through line 16. The pressure in reactor 22 will be lower than the pressure in reactor 10, since approximately 10 percent of the gas feed which was converted to alcohols in reactor 10 is no longer present in the gas stream. The pressure is also reduced because of pressure losses in the lines and vessel between reactors 10 and 22. Additional heat may or may not be necessary to maintain the desired reaction temperature in reactor 22. While heat will be lost from the system, the hydration reaction is exothermic, which adds heat to the system. In any event, if additional heat is required, it can be provided by heat exchanger 20 with a suitable source of heat such as steam.

In reactor 22, the olefin feed gases are brought in contact with the polymer catalyst to effect conversion of about 1 to about 25 percent of the olefins remaining in this gas. Effluent from reactor 22 is introduced to vessel 28 through line 26. Ethanol and isopropanol again are dissolved in water and removed from vessel 28 through line 38. As necessary, makeup water to the system may be introduced to vessel 28 from line 30. The olefin containing feed gas, reduced still further in pressure, is removed from vessel 28 through line 32 and passed to reactor 36. As needed, heat may be introduced to this gas in Heater 34.

A similar reaction to those previously described takes place in reactor 36, whereby additional ethylene and propylene are converted to alcohols. The effluent from this reactor exits through line 40 and enters vessel 42 where alcohols are again dissolved in water and removed from the system through line 50. The effluent from vessel 42 is removed and introduced to another reactor 52, wherein the hydration of olefins to alcohols takes place in the same manner as previously described. Effluent from reactor 52 is introduced to vessel 56 through line 54. Alcohols again are dissolved in water and removed from vessel 56 through line 58.

The alcohol products recovered from the four reactors through lines 24, 38, 50, and 58 may be combined and removed from the unit through line 60. These alcohols can subsequently be processed to remove the water and separate the alcohols into individual products as desired.

The olefin feed gas now substantially depleted in olefin content may be removed from vessel 56 through line 62 and utilized for fuel or discarded.

The process is shown as being carried out in a series of four reactors; however, there is no limit on the number of reactors which can be used which becomes solely a matter of economics as the olefin content of the feed gas is depleted. In order to provide a substantial and economic yield of alcohol products, the process is carried out in a minimum of three reactors and preferably in 4 or more reactors.

The following examples are presented in illustration of the invention.

EXAMPLE 1

A feed gas containing 7.5 percent ethylene and 3 percent propylene with the balance being methane and hydrogen was contacted with Nafion ® NR50 catalyst, a perfluorinated ion-exchange polymer with a fluorocarbon polymer backbone and side chain with a pendant sulfonic acid site on the end of the side chain. The equivalent weight of the polymer was about 1,100, that is one acid site for every 1,100 molecular weight units. The molecular weight of the polymer was between 10,000 and 100,000. Several runs were made with 100 percent catalyst. In the other runs, the catalyst percentage ranged from 1.94 to 2.9 percent catalyst deposited on shot coke. The runs were carried out at temperatures of 428° F. and 455° F. at a pressure of 1,000 psig and a WHSV ranging from 1.1 to 109 cc of gas feed per minute per gram of polymer catalyst.

The hydration runs were carried out in the vapor phase, and the feed gas was pressured directly from a gas cylinder/regulator through a metering valve into a water saturator vessel. The feed was then passed downflow through a ⅜-inch coiled tubing reactor 20 feet long. A sand bath was used to keep the saturated vessel/reactor coil at a constant temperature. The reactor products passed through a two-stage back pressue regulator system before entering an absorber filled with distilled water. This absorber removed the alcohol products, and samples were withdrawn from it for analysis. The gas leaving the absorber passed through a wet test meter, which was used for determining dry gas flow rates. The runs were allowed to proceed for at least two days, since it took about one day for the catalyst to become saturated with alcohol. The operating conditions employed in the runs and the present conversion of ethylene to ethanol and propylene to isopropanol are shown in Table 1.

TABLE 1

| Run No. | Temp. °F. | Pressure psig | Catalyst Percent Polymer | WHSV* | PERCENT CONVERSION | |
|---|---|---|---|---|---|---|
| | | | | | Ethylene to Ethanol | Propylene to Isopropanol |
| 1 | 455 | 1,000 | 100 | 1.1 | 6.4 | 0.9 |
| 2 | 455 | 1,000 | 100 | 3.5 | 6.5 | 1.3 |
| 3 | 455 | 1,000 | 100 | 11 | 6.2 | 2.3 |
| 4 | 455 | 1,000 | 100 | 36 | 5.3 | 4.5 |
| 5 | 455 | 1,000 | 100 | 67 | 1.2 | 4.5 |
| 6 | 455 | 1,000 | 2.5 | 18 | 6.2 | 2.6 |
| 7 | 455 | 1,000 | 2.5 | 53 | 7.0 | 3.5 |
| 8 | 455 | 1,000 | 2.5 | 109 | 4.8 | 3.8 |
| 9 | 455 | 1,000 | 100 | 1.7 | 5.8 | 4.7 |
| 10 | 455 | 1,000 | 2.5 | 17.9 | 5.7 | 4.0 |
| 11 | 455 | 1,000 | 1.94 | 14 | 5.0 | 7.4 |
| 12 | 428 | 1,000 | 2.5 | 8.4 | 3.5 | 4.7 |
| 13 | 428 | 1,000 | 2.9 | 5.3 | 3.9 | 2.9 |

*cc of dry gas feed/minute/gm of polymer catalyst

It is noted from the table that the percent conversion to ethanol and isopropanol varied from about 0.9 to as high as 7.4 percent, depending on the particular olefin and the operating conditions employed. It is further noted that the percent conversion obtained with 100 percent polymer did not differ in magnitude from that obtained with the polymer deposited on shot coke.

EXAMPLE 2

An FCC tail gas containing 15 percent ethylene and 6 percent propylene is contacted with pure pelleted Nafion NR50 catalyst disposed in a series of reactors as shown in the multireactor drawing previously described. The operating conditions employed, the composition of the feed gas to and the effluent gas from each reactor, and the percent ethylene and propylene converted to alcohols in each reactor is summarized in Table 2.

TABLE 2

| Reactor No. | Press. psig | Temp. °F. | FEED GAS | | EFFLUENT GAS | | PERCENT OLEFIN CONVERTED TO ALCOHOL | | WHSV* #/Hr/# |
|---|---|---|---|---|---|---|---|---|---|
| | | | % C$_2$= | % C$_3$= | % C$_2$= | % C$_3$= | % C$_2$OH | % C$_3$OH | |
| 10 | 1200 | 455 | 15 | 6 | 14.1 | 5.6 | 6 | 7 | 30 |
| 22 | 1175 | 455 | 14.1 | 5.6 | 13.2 | 5.2 | 6 | 7 | 30 |
| 36 | 1150 | 455 | 13.2 | 5.2 | 12.4 | 4.8 | 6 | 7 | 30 |
| 52 | 1125 | 455 | 12.4 | 4.8 | 11.7 | 4.5 | 6 | 7 | 30 |

*cc of dry gas feed/min/gm of polymer catalyst.

TOTAL OLEFIN CONVERSION IN FOUR REACTORS

Ethylene 22%
Propylene 25%

It is noted from the table that the pressure in each reactor is reduced due to pressure drop in the system and to conversion of olefins to the alcohols and the removal of such alcohols. The amount of ethylene and proylene in each progressive feed gas and effluent gas is also reduced for the same reason as is the space velocity in each succeeding reactor.

The reactor configuration used allows basically unlimited conversion of olefins to the alcohols. The number of reactors in series used is limited only by the economics of the reduced quantities of alcohol produced in each succeeding reactor.

While certain embodiments and details have been shown for the purpose of illustrating the present invention, it will be apparent to those skilled in the art that various changes and modifications may be made herein without departing from the spirit or scope of the invention.

I claim:

1. A process for converting olefins to alcohols which comprises the steps of:
   (a) contacting a feed gas containing an olefin selected from the group consisting of ethylene, propylene, butylene, or pentylene and mixtures thereof with a perfluorinated ion-exchange polymer catalyst under vapor phase reaction conditions in a first reaction zone, wherein from about 1 to about 20 weight percent of said olefins are converted to alcohols;
   (b) contacting effluent gases from the first reaction zone with water whereby alcohols are extracted from said gases in water solution;
   (c) contacting the extracted effluent gases from the first reaction zone with additional perfluorinated ion-exchange catalyst under vapor phase reaction conditions in a second reaction zone connected in series with the first reaction zone whereby from about 1 to about 20 weight percent of said olefins in the extracted effluent gases are converted to alcohols;
   (d) contacting effluent gases from the second reaction zone with water whereby alcohols are extracted from said gases in water solution;
   (e) contacting the extracted effluent gases from the second reation zone with additional perfluorinated ion-exchange catalyst under vapor phase reaction conditions in a third reaction zone connected in series with the first and second reaction zones whereby from about 1 to about 20 weight percent of said olefins in the extracted effluent gases are converted to alcohols;
   (f) contacting effluent gases from the third reaction zone with water whereby alcohols are extracted from said gases in water solution; and
   (g) recovering the alcohol products from each reaction zone.

2. The process of claim 1 wherein the feed gas to the first reaction zone contains a mixture of ethylene and propylene.

3. The process of claim 1 wherein the feed gas is a tail gas from a fluid catalyst cracking unit.

4. The process of claim 3 wherein the feed gas is a tail gas from a fluid catalyst cracking unit which contains from about 10 to 20 weight percent ethylene and from about 4 to 10 weight percent propylene.

5. The process of claim 1 wherein the catalyst is a perfluorinated ion-exchange polymer supported on a substrate, wherein the surface of said substrate is hydrophobic.

6. The process of claim 5 wherein the substrate is calcined shot coke.

7. The process of claim 1 wherein the vapor phase reaction conditions for the first, second and third reaction zones comprise a temperature of from about 250° F. to about 475° F., a pressure of from about 200 psig to about 4,000 psig and a weight hourly space velocity of from about 1 to about 2,000 cubic centimeters of total dry gas feed per minute per gram of catalyst.

8. A process for converting olefins to alcohols which comprises contacting a feed gas comprising a mixture of ethylene and propylene with a perfluorinated ion-exchange polymer catalyst under vapor pressure reaction conditions in three separate reaction zones connected in series.

9. The process according to claim 8 wherein the feed gas to the reaction zones is a tail gas from a fluid catalyst cracking unit.

10. The process according to claim 8 wherein the feed gas contains from about 10 to about 20 weight percent ethylene and from about 4 to about 10 weight percent propylene.

11. The process according to claim 8 wherein the catalyst is a perfluorinated ion-exchange polymer supported on a substrate.

12. The process according to claim 11 wherein the surface of the substrate is hydrophobic.

13. The process according to claim 11 wherein the substrate is calcined shot coke.

14. The process according to claim 8 wherein the perfluorinated ion-exchange polymer has an equivalent weight of from about 500 to about 20,000.

15. The process according to claim 8 wherein the perfluorinated ion-exchange polymer has an equivalent weight of from about 600 to about 2,000.

16. The process according to claim 8 wherein the vapor phase reaction conditions comprise a temperature of from about 250° F. to about 475° F., a pressure of from about 200 psig to about 4,000 psig and a weight hourly space velocity of from about 1 to about 2,000 cubic centimeter of total dry gas feed per minute per gram of catalyst.

17. The process according to claim 8 wherein gas effluent from the first reaction zone is contacted with water whereby alcohols are extracted from said gas in water solution.

18. The process according to claim 8 wherein gas effluent from the second reaction zone is contacted with water whereby alcohols are extracted from said gas in water solution.

19. The process according to claim 8 wherein gas effluent from the third reaction zone is contacted with water whereby alcohols are extracted from said gas in water solution.

* * * * *